US008853436B2

(12) United States Patent
Portilho et al.

(10) Patent No.: US 8,853,436 B2
(45) Date of Patent: Oct. 7, 2014

(54) HETEROGENEOUS CATALYSTS FOR TRANSESTERIFICATION OF TRIGLYCERIDES AND PREPARATION METHODS OF SAME

(71) Applicant: Petroleo Brasileiro S.A.-Petrobras, Rio De Janeiro (BR)

(72) Inventors: Márcio de Figueiredo Portilho, Niterói (BR); Alexander Rangel Bastos, São João de Meriti (BR)

(73) Assignee: Petroleo Brasileiro S.A.-Petrobras, Rio de Janeiro (BR)

( * ) Notice: Subject to any disclaimer, the term of this patent is extended or adjusted under 35 U.S.C. 154(b) by 0 days.

(21) Appl. No.: 14/057,252

(22) Filed: Oct. 18, 2013

(65) Prior Publication Data
US 2014/0046082 A1 Feb. 13, 2014

Related U.S. Application Data

(62) Division of application No. 12/588,678, filed on Oct. 23, 2009, now abandoned.

(30) Foreign Application Priority Data

Dec. 29, 2008 (BR) ..................................... 0805625

(51) Int. Cl.
*C07C 67/02* (2006.01)
*C11C 3/10* (2006.01)
*B01J 21/04* (2006.01)
*B01J 27/18* (2006.01)
*B01J 23/02* (2006.01)
*C11C 3/00* (2006.01)

(52) U.S. Cl.
CPC ............. *C07C 67/02* (2013.01); *B01J 27/1806* (2013.01); *B01J 23/02* (2013.01); *Y02E 50/13* (2013.01); *C11C 3/003* (2013.01)

USPC ........... 554/163; 554/167; 554/168; 554/169; 554/124; 252/182.12; 502/208; 502/232; 502/246; 502/340; 502/353

(58) Field of Classification Search
None
See application file for complete search history.

(56) References Cited

U.S. PATENT DOCUMENTS

| 2,091,988 | A | * | 9/1937 | Hubbuch et al. ............... 554/164 |
|---|---|---|---|---|
| 2,634,234 | A | * | 4/1953 | Kuhrt ............................... 203/88 |
| 3,525,599 | A | * | 8/1970 | Nield ............................... 44/372 |
| 3,806,454 | A | * | 4/1974 | Sias-Roy-C. .................. 508/402 |
| 5,075,275 | A | | 12/1991 | Murakami et al. |
| 5,908,946 | A | | 6/1999 | Stern et al. |
| 5,958,829 | A | | 9/1999 | Domesle et al. |
| 6,350,421 | B1 | | 2/2002 | Strehlau et al. |
| 7,728,181 | B2 | | 6/2010 | Kouka et al. |
| 2002/0042342 | A1 | | 4/2002 | Mussmann et al. |
| 2004/0102655 | A1 | | 5/2004 | Liang et al. |
| 2005/0014237 | A1 | | 1/2005 | Lee |
| 2006/0257982 | A1 | | 11/2006 | Binder et al. |
| 2008/0021232 | A1 | * | 1/2008 | Lin et al. ....................... 554/174 |
| 2009/0227818 | A1 | | 9/2009 | Kouka et al. |
| 2010/0163793 | A1 | * | 7/2010 | Portilho et al. ........... 252/182.12 |

FOREIGN PATENT DOCUMENTS

| WO | WO 2005/021697 | 3/2005 |
|---|---|---|
| WO | WO 2007/086496 | 8/2007 |

OTHER PUBLICATIONS

Mohadesi et al., "Biodiesel production using alkali earth metal oxides catalysts synthesized by sol-gel method", Biofuel Research Journal, 1 (2014), pp. 30-33.

* cited by examiner

Primary Examiner — Joseph D Anthony
(74) Attorney, Agent, or Firm — Nixon & Vanderhye P.C.

(57) ABSTRACT

Method for transesterification of fatty acid esters. The method includes contacting (i) a catalyst comprising at least one of barium oxide and apatite with (ii) a reaction medium comprising at least one of vegetable oil and fats.

7 Claims, No Drawings

HETEROGENEOUS CATALYSTS FOR TRANSESTERIFICATION OF TRIGLYCERIDES AND PREPARATION METHODS OF SAME

CROSS-REFERENCE TO PRIOR APPLICATIONS

This application is a continuation of U.S. patent application Ser. No. 12/588,678, filed Oct. 23, 2009, currently pending, which claims priority to Brazilian Patent Application No. PI 0805625-0, filed 29 Dec. 2008, the entire contents of each of which are hereby incorporated by reference.

FIELD OF THE INVENTION

This invention belongs to the field of catalysts for the transesterification of triglycerides, for the production of fatty acid glycerin and esters. More specifically, the invention describes solid catalysts for heterogeneous transesterification of triglycerides present in oils and fats and preparatory methods for the production of same. The solid catalysts of this invention are sufficiently magnetic to use in the production of biodiesel from vegetable oils and fats, not only because they work in a similar fashion as state of the art catalysts, but also because of the low cost of the raw materials used in its production.

FUNDAMENTALS OF THE INVENTION

Since the middle of the last century, much research has been carried out to search for alternative technologies to produce fuels from renewable sources or industrial waste products.

Transesterfication or alcoholization appeared to be a significantly advantageous industrial procedure to make it feasible to obtain fuel from triglycerides, present in vegetable oils and fats. Methanol was used, or alternatively ethanol, in the presence of homogeneous alkaline catalysts to generate long chain esters and glycerin. However, transesterfication using homogeneous catalysts introduces problems. Normally, the catalyst must be removed through complicated separation processes which increase the price of the final products. Moreover, alkaline catalysts cause saponification of the free fatty acid esters present in oils, which requires the products to be washed with enormous amounts of water and causing a reduction in the ester production.

The impurity of the products obtained as well as burning of fuel generates considerable amounts of formaldehyde, acrylaldehyde, the metallic salts of formic acid and carbonates, in addition to pollutants cause damage to pistons and engines.

In recent studies on the processing of vegetable oil published in scientific and patent literature, the state of the art shows that there is always a concern regarding how to prevent the formation of undesirable by-products, that requires purification using a distillation stage and which makes industrial production financially unattractive.

Biodiesel synthesis using solid catalysts (heterogeneous) is more complex and the mechanisms involved are little understood.

U.S. Pat. No. 5,908,946 describes a process to produce fuel from vegetable or animal oils, using a heterogeneous catalyst to carry out the alcoholization. The catalyst includes a mixture of zinc and aluminum oxides. The process also produces pure glycerin.

Patent WO 2005/021697 A1 describes a method to produce glycerin and long chain esters, suitable for use in biodiesel, both having a high level of purity.

Transesterification with alcohol is carried out from oils and fats using a heterogeneous catalyst that may include an oxide, an alkaline metal and at least one metal element selected from among groups 4 and 5 of the periodical table of chemical elements, associated with H, Ti, and Nb or Ta.

SUMMARY OF THE INVENTION

This invention describes preparatory methods using solid catalysts and the formulation of these catalysts for the production of fatty acid esters, glycerin, and specifically, biodiesel through the heterogeneous transesterification reaction of triglycerides present in vegetable oils and fats, such as soy, cotton seed, canola, castor, peanut oils and animal fats. A conversion of 100% is obtained using catalysts prepared using the procedures described in this invention. The purity of the products, such as biodiesel and glycerin, in the composition produced is greater than 96.5%. The catalysts of this invention are economically obtained from cheaper raw materials and lower industrial costs of production, making them more attractive for production on a large scale than the catalysts produced by other methods for the same purpose.

DETAILED DESCRIPTION OF THE INVENTION

This invention describes catalysts for the heterogeneous transesterification of triglycerides present in vegetable oils and fats. The catalysts consist of:
   a) one solid oxide or a mixture of solid oxides;
   b) a solid substrate.

The invention also describes preparatory methods for these catalysts. The invention even describes a composition that includes not less than 98% p/p of fatty acid esters and no more than 4,500 ppm of fatty acids. The purity of the products, such as biodiesel and glycerin, is greater than 96.5%.

The catalysts may be used with vegetable oil as well as soy oil, cottonseed oil, canola oil, castor oil, peanut oil, as well as pure or used animal fat. The solid oxide is apatite or a barium oxide. The substrate consists of a solid oxide or a mixture of solid oxides, that confers suitable textural properties to said catalyst and improves its catalytic performance such as for example, an alumina. These catalysts are more active in the production of biodiesel than the catalysts used in other state of the art processes. The two preparatory methods presented below are procedures that should not be considered to be, under any circumstances, a limiting or restricting factor on the originality of this invention.

Procedure for Preparing the Apatite Catalyst

The apatite catalyst is obtained from the powdered ore of same name, with an enriched phosphorus level, using the traditional treatment for phosphoric acid production. The resulting powder is dried in a kiln at 120° C./16 hr and later heated at 550° C./3 hr. The apatite thus produced has the following elemental composition: Phosphorus, 4.1%; barium, 10.0%; calcium, 6.1%; iron, 9.0%; manganese, 1.3%; aluminum, 11.0%.

Procedure for Preparing the Barium Oxide Catalyst

The barium oxide catalyst is prepared from a mixture containing 80% gamma-aluminum and 20% barium hydroxide octahydrate. The mixture is peptized using the wet point technique with an acetic acid solution of 4% p/p. After that it is dried at 120° C./8 hr and is heated to 550° C./3 hr.

EXAMPLES

As can be seen in the examples below the production of biodiesel from vegetable oils and fats reach a 100% conversion in one step, through the method describe in this invention. The reaction conditions for obtaining biodiesel with the use of these catalysts make use of temperatures lower than 290° C., under self-generated system pressure. The reaction may be carried out using the batch or continuous mode. The catalyst is added to the reagent oil in amounts that fall within the range of 1% p/p and 5% p/p. The heated reaction medium is maintained at the reaction temperature during an interval of time that falls in the range of between 1 and 8 hours. Separation of the catalyst is accomplished by filtration. The alcohol/glycerin mixture is separated from the biodiesel mixture by gravimetric or centrifugal decanting. The biodiesel is washed with water, to remove fine residual catalyst and alcohol particles and then it is dried.

In the examples below, transesterification reactions are performed in the reactor in batches of 300 ml, under self-generated system pressure, mechanical mixing at 500 rpm and the oil/alcohol ratio is 1/15 mol/mol and 130 mol/mol, respectively. The product yield is measured by nuclear magnetic carbon 13 resonance ($RMN^{13}C$), the reaction time and the amount of catalyst are shown in each example. Analysis by atomic absorption to detect alkaline and alkaline-earth metals, phosphorus and aluminum in the reaction products, resulted to be below the detection limit, confirming in this way the heterogeneous catalyst. Reactions were performed using conventional catalytic solids under the same conditions as the reaction conditions shown in the examples, the yield of which shall be used as a reference for the yield achieved by this invention.

Example 1

Experiment performed in a reactor in batches, with sampling of 2 in 2 hours.
=Conditions of the Experiment: 100 grams of canola oil; 50 grams of methanol (molar ratio of oil/alcohol, 1/15); 1 g of apatite catalyst.
=Reaction Conditions: 175° C./8 hr in a single stage and at self-generated pressure.
=Conversion of 95.06% of oil, 88.10% in methyl esters and 2.90% in mono- and diglycerides.
=Reference: Conversion of 45.43% of oil, 37.93% in methyl esters and 7.5% in mono- and diglycerides.

Example 2

Experiment performed in a reactor in batches, with sampling of 2 in 2 hours.
=Conditions of the Experiment: 100 grams of canola oil; 100 grams of methanol (molar ratio of oil/alcohol, 1/30); 1 g of apatite catalyst.
=Reaction Conditions: 175° C./8 hr in a single stage and at self-generated pressure.
=Conversion of 98.00% of oil, 95.10% in methyl esters and 2.90% in mono- and diglycerides.

Example 3

Experiment performed in a reactor in batches, with sampling of 2 in 2 hours.
=Conditions of the Experiment: 100 grams of soy oil; 100 grams of methanol (molar ratio of oil/alcohol, 1/30); 1 g of apatite catalyst.
=Reaction Conditions: 175° C./8 hr in a single stage and at self-generated pressure.
=Conversion of 100% of oil, 98.03% in methyl esters and 1.97% in mono- and diglycerides.

Example 4

Experiment performed in a reactor in batches, with sampling of 2 in 2 hours.
=Conditions of the Experiment: 100 grams of sunflower seed oil; 100 grams of methanol (molar ratio of oil/alcohol, 1/30); 1 g of apatite catalyst.
=Reaction Conditions: 175° C./8 hr in a single stage and at self-generated pressure.
=Conversion of 100% of oil, 98.19% in methyl esters and 1.81% in mono- and diglycerides.

Example 5

Experiment performed in a reactor in batches, with sampling of 2 in 2 hours.
=Conditions of the Experiment: 100 grams of corn oil; 100 grams of methanol (molar ratio of oil/alcohol, 1/30); 1 g of apatite catalyst.
=Reaction Conditions: 175° C./8 hr in a single stage and at self-generated pressure.
=Conversion of 100% of oil, 98.37% in methyl esters and 1.63% in mono- and diglycerides.

Example 6

Experiment performed in a reactor in batches, with sampling of 60 in 60 hours.
=Conditions of the Experiment: 100 grams of canola oil; 50 grams of methanol (molar ratio of oil/alcohol, 1/15); 1 g of apatite catalyst.
=Reaction Conditions: 200° C./3 hr in a single stage and at self-generated pressure.
=Conversion of 100% of oil, 95.77% in methyl esters and 4.23% in mono- and diglycerides.

Example 7

Experiment performed in a reactor in batches, with sampling of 60 in 60 hours.
=Conditions of the Experiment: 100 grams of castor oil; 50 grams of methanol (molar ratio of oil/alcohol, 1/15); 1 g of apatite catalyst.
=Reaction Conditions: 200° C./3 hr in a single stage and at self-generated pressure.
=Conversion of 97.93% of oil, 91.32% in methyl esters and 6.61% in mono- and diglycerides.

Example 8

Experiment performed in a reactor in batches, with sampling of 60 in 60 hours.
=Conditions of the Experiment: 100 grams of sunflower seed oil; 50 grams of methanol (molar ratio of oil/alcohol, 1/15); 1 g of apatite catalyst.
=Reaction Conditions: 200° C./3 hr in a single stage and at self-generated pressure.
=Conversion of 100% of oil, 95.78% in methyl esters and 4.22% in mono- and diglycerides.

Example 9

Experiment performed in a reactor in batches, with sampling of 60 in 60 hours.

=Conditions of the Experiment: 100 grams of palm oil; 50 grams of methanol (molar ratio of oil/alcohol, 1/15); 1 g of apatite catalyst.
=Reaction Conditions: 200° C./3 hr in a single stage and at self-generated pressure.
=Conversion of 100% of oil, 94.60% in methyl esters and 5.40% in mono- and diglycerides.

Example 10

Experiment performed in a reactor in batches, with sampling of 60 in 60 hours.
=Conditions of the Experiment: 100 grams of corn oil; 50 grams of methanol (molar ratio of oil/alcohol, 1/15); 1 g of apatite catalyst.
=Reaction Conditions: 200° C./3 hr in a single stage and at self-generated pressure.
=Conversion of 100% of oil, 95.77% in methyl esters and 4.23% in mono- and diglycerides.

Example 11

Experiment performed in a reactor in batches, with sampling of 60 in 60 hours.
=Conditions of the Experiment: 100 grams of canola oil; 100 grams of methanol (molar ratio of oil/alcohol, 1/30); 1 g of apatite catalyst.
=Reaction Conditions: 200° C./3 hr in a single stage and at self-generated pressure.
=Conversion of 100% of oil, 99.08% in methyl esters and 0.92% in mono- and diglycerides.

Example 12

Experiment performed in a VINCI unit under continuous flow. The catalyst was charged with barium oxide, in accordance with the procedure described by the manufacturer. A constant temperature was maintained during the process. The flow of the reagents is maintained so that the canola oil/methyl alcohol molar ratio, 1/27 mol/mol is not altered. The level of biodiesel is determined in the samples collected during the following time periods: 15.5 hours—100%; 19.2 hours—99.28%; 21.5 hours—99.29%; 24.5 hours—99.06%; 39 hours—98.03%. The variation in the level of biodiesel in the product is within the margin of error of the $RMN^{13}C$ analysis, estimated at 2%. The results indicate that the conversion was not reduced as a function of the reaction time within the range studied.

Example 13

Experiment performed in a reactor in batches. In this reaction the catalyst from Example 12 is reused, for the purpose of checking whether it is deactivated in a continuous test.
=Conditions of the Experiment: 100 grams of canola oil; 50 grams of methanol; 1 g of barium oxide catalyst.
=Reaction Conditions: 200° C./3 hr in a single stage and at self-generated pressure.
=Conversion of 99.19% of oil, 95.25% in methyl esters and 3.94% in mono- and diglycerides.
=Reference: Conversion of 45% of oil, 40.5% in methyl esters and 4.5% in mono- and diglycerides.

The invention claimed is:

1. A method for transesterification of fatty acid esters, the method comprising the following steps: contacting (i) a catalyst comprising at least one catalyst chosen from the group consisting of barium oxide supported on alumina and apatite with (ii) a reaction medium comprising at least one reagent oil chosen from the group consisting of vegetable oil and fats.

2. The method according to claim 1, wherein the vegetable oil is chosen from the group consisting of soy oil, cotton seed oil, canola oil, castor oil, peanut oil, and mixtures thereof.

3. The method according to claim 1, wherein the reaction medium further comprises at least one alcohol chosen from the group consisting of methanol and ethanol.

4. The method according to claim 1, wherein the contacting step has a duration of between 1 and 8 hours.

5. The method according to claim 1, wherein the contacting step occurs at a temperature less than 290° C.

6. The method according to claim 1, wherein a ratio of the at least one catalyst to the at least one reactant oil is in a range between 1% p/p and 5% p/p.

7. The method according to claim 3, wherein a ratio of the at least one reactant oil to the at least one alcohol is in a range between 1/15 mol/mol and 130 mol/mol.

* * * * *